United States Patent

Vigna et al.

[11] Patent Number: 6,051,854
[45] Date of Patent: Apr. 18, 2000

[54] INTEGRATED SEMICONDUCTOR DEVICE COMPRISING A CHEMORESISTIVE GAS MICROSENSOR AND MANUFACTURING PROCESS THEREOF

[75] Inventors: Benedetto Vigna, Potenza; Paolo Ferrari, Gallarate; Ubaldo Mastromatteo, Cornaredo, all of Italy

[73] Assignee: STMicroelectronics S.r.l., Agrate Brianza, Italy

[21] Appl. No.: 09/089,816

[22] Filed: Jun. 3, 1998

[30] Foreign Application Priority Data

Jun. 4, 1997 [EP] European Pat. Off. .............. 97830272

[51] Int. Cl.[7] ................................................. H01L 23/58
[52] U.S. Cl. ..................... 257/252; 257/253; 257/414; 438/49; 204/424; 204/426; 204/431
[58] Field of Search ................................ 257/414, 252, 257/253; 438/49; 204/424, 426, 431

[56] References Cited

U.S. PATENT DOCUMENTS

| | | | |
|---|---|---|---|
| 4,862,197 | 8/1989 | Stoffel | 346/140 R |
| 4,984,446 | 1/1991 | Yagawara et al. | 73/31.06 |
| 5,236,569 | 8/1993 | Murase et al. | 204/412 |
| 5,434,551 | 7/1995 | Chen et al. | 338/34 |
| 5,447,618 | 9/1995 | Sugiyama et al. | 204/426 |
| 5,545,300 | 8/1996 | Yun et al. | 204/424 |
| 5,787,866 | 8/1998 | Sugiyama et al. | 123/672 |
| 5,976,335 | 11/1999 | Kato et al. | 204/425 |
| 5,976,350 | 11/1999 | Yamada et al. | 205/784.5 |

FOREIGN PATENT DOCUMENTS

| | | |
|---|---|---|
| 63-205554 | 8/1988 | Japan. |
| 407260728 | 10/1995 | Japan. |
| 411051893 | 2/1999 | Japan. |
| WO 95/10770 | 4/1995 | WIPO. |

OTHER PUBLICATIONS

Stoffel, Axel M., "Micromachining and ASIC technology" *Microelectronics Journal*, May 25 1994 pp. 145–156.

*Primary Examiner*—William Mintel
*Attorney, Agent, or Firm*—Theodore E. Galanthay; Robert Iannucci; Seed IP Law Group PLLC

[57] ABSTRACT

An integrated semiconductor device comprises, reciprocally superimposed, a thermally insulating region; a thermal conduction region of a high thermal conductivity material; a passivation oxide layer; and a gas sensitive element. The thermal conduction region defines a preferential path towards the gas sensitive element for the heat generated by the heater element, thereby the heat dispersed towards the substrate is negligible during the operation of the device.

12 Claims, 1 Drawing Sheet

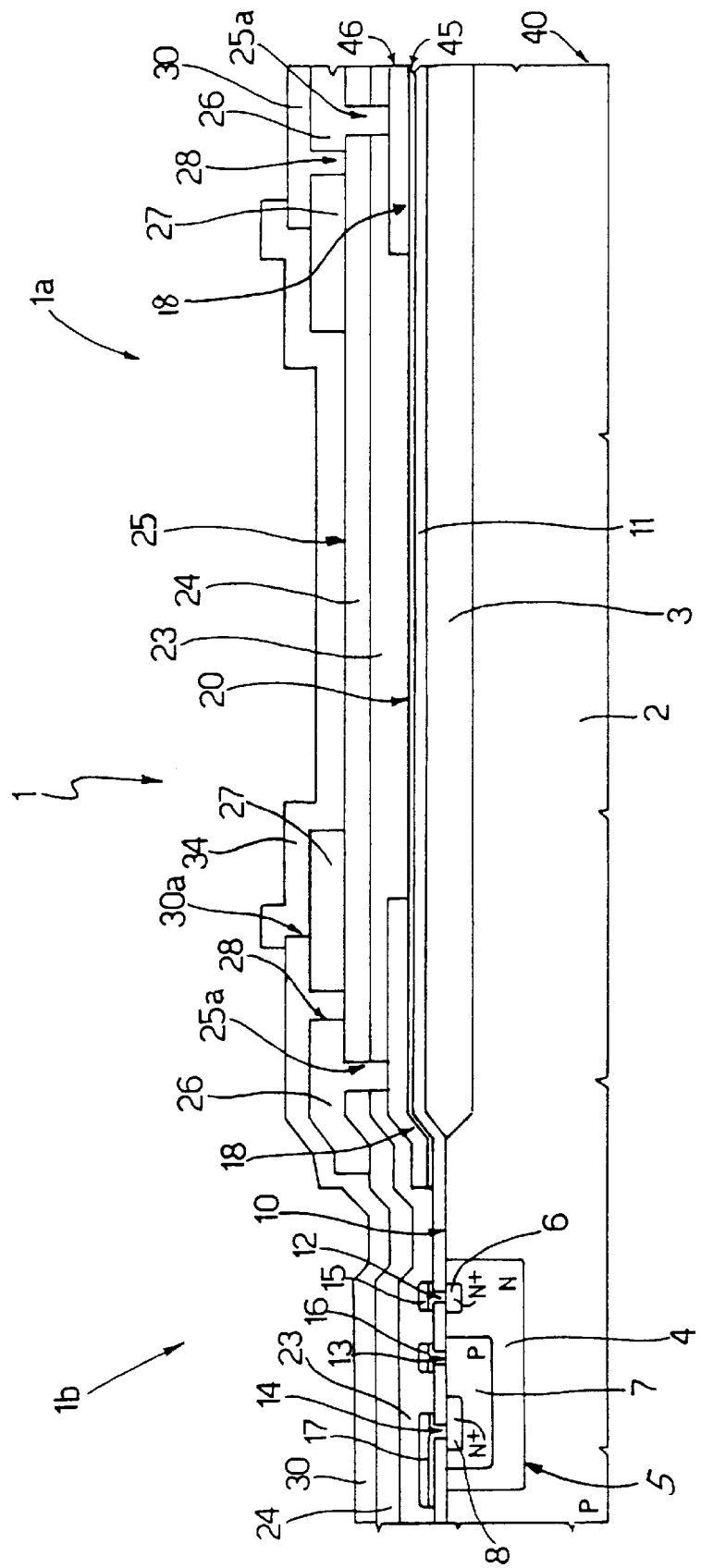

INTEGRATED SEMICONDUCTOR DEVICE COMPRISING A CHEMORESISTIVE GAS MICROSENSOR AND MANUFACTURING PROCESS THEREOF

TECHNICAL FIELD

The invention relates to an integrated semiconductor device comprising a chemoresistive gas microsensor and an associated manufacturing process.

BACKGROUND OF THE INVENTION

As is known, chemical sensors detect the presence of gas thanks to a chemical reaction which takes place between molecules of the gas and a sensitive film. The chemical reaction depends significantly on an operating temperature which influences the effects of adsorption, desorption and diffusion of the gas in the film. Consequently, temperature is an important factor in optimizing the performance of the sensors, particularly as regards sensitivity, selectivity and response time. To obtain an optimum operation, therefore, the sensors are provided with means for regulating and controlling temperature.

Recently, integrated chemoresistive gas microsensors, the manufacture of which makes use of microelectronics techniques, have been proposed and produced. These microsensors have the following advantages: reduced manufacturing costs, low energy consumption in operation, short response times and integrability with a temperature control and output signal processing circuit.

Integrated gas microsensors using chemoresistive films based on tin oxide have appeared on the market. On the surfaces of such films, deposited on a wafer of semiconductor material machined using a technique of "bulk micromachining", described below, a chemical reaction takes place between oxygen of the film and the gas to be detected which has an effect of changing the resistance of the film and thus enables the presence of the gas to be detected.

In view of the fact that in order to operate correctly, such sensors must be maintained at temperatures of approximately 400° C., they are provided with heater elements and must be thermally insulated from the rest of the chip integrating a signal processing and control circuit.

Various techniques for isolating the sensitive film from the rest of the chip are known in literature. The technique used historically is that of "bulk micromachining", which includes producing the sensitive film on top of or inside a dielectric layer deposited on a massive silicon wafer and of removing a portion of massive silicon from the back of the wafer with wet etching methods. The dielectric layer performs a dual task of mechanically supporting the sensor and thermally insulating the sensor from the massive silicon wafer. In the context of this technique, prototypes have been produced with partial removal of the silicon from the area of the sensor, in which the excavation is carried out only on part of the thickness of the wafer, and prototypes which provide the total removal of the silicon in correspondence with the area of the sensor (the etching reaches as far as the dielectric layer carrying the sensor element). As regards this second solution, reference may be made for example to the article entitled "Basic Micro-Module for chemical sensors with on chip heater and buried sensor structure" by D. Mutschall, C. Scheibe, E. Obermeier.

On the other hand, the technique of bulk micromachining requires the presence of front-back machining processes and comprises particular demands for handling the chips which are such that it proves to be incompatible with current integrated circuit manufacturing methods.

Another proposed technique includes "front micromachining" on the basis of which the massive silicon wafer is etched from the front and a dielectric layer mechanically supports and thermally insulates the sensor element. In this respect, for manufacturing a different type of sensor, reference may be made for example to the article by D. Moser and H. Baltes entitled "A high sensitivity CMOS gas flow sensor based on an N-poly/P-poly thermopile", DSC-Vol. 40, *Micromechanical Systems,* ASME, 1992; furthermore, for a survey of the techniques of bulk and front micromachining, reference may also be made to the article entitled "Micromachining and ASIC technology" by Axel M. Stoffel in *Microelectronics Journal,* 25 (1994), pages 145–156.

In this case also, the technique for producing suspended structures requires the use of etching steps that are not very compatible with the current manufacturing processes used in microelectronics and does not therefore permit sensors and the related control and processing circuitry to be obtained on a single chip.

Furthermore, the use of dedicated SOI (Silicon-On-Insulator) substrates has been proposed, in which the starting wafer comprises a stack of silicon/silicon oxide/silicon, with the oxide selectively removed at the sensor area, forming an air gap. The excavations made from the front of the wafer at the end of the process steps to produce the air gap and enable the sensor to be thermally insulated. In this respect, for a shear stress sensor, reference may be made for example to the article by J. Shajii, Kay-Yip Ng and M. A. Schmidt entitled "A Microfabricated Floating-Element Shear Stress Sensor Using Wafer-Bonding Technology", *Journal of Microelectromechanical Systems,* Vol. 1, No. 2, Jun. 1992, pages 89–94. A method used for bonding (apart from forming the air gap) is further described in the article "Silicon-on-Insulator Wafer Bonding-Wafer Thinning Technological Evaluations" by J. Hausman, G. A. Spierings, U. K. P. Bierman and J. A. Pals, *Japanese Journal of Applied Physics,* Vol. 28, No. 8, August 1989, pages 1426–1443.

SUMMARY OF THE INVENTION

An object of the invention is to provide a manufacturing process and a chemoresistive gas sensor which do not have the disadvantages of the current techniques, and in particular which do not require excavation operations in the silicon.

In an embodiment of the invention, an integrated device comprising a chemoresistive gas microsensor and a process for manufacturing an integrated semiconductor device comprising a chemoresistive gas microsensor are provided.

In particular, one embodiment is a semiconductor chemical sensor device comprising a semiconductor substrate, a patterned dielectric layer deposited over the semiconductor substrate, a heater element deposited over a portion of the dielectric layer, a high thermal conductivity element deposited at least over the heater element, and a chemical sensitive element deposited over part of the high thermal conductivity element.

For an understanding of the invention, features and advantages of a preferred embodiment will now be described, purely by way of non-exhaustive example, with reference to the accompanying drawing.

BRIEF DESCRIPTION OF THE DRAWING

FIG. 1 shows the cross-section of the integrated device according to the invention.

DETAILED DESCRIPTION OF THE INVENTION

With reference to FIG. 1, an integrated semiconductor device 1 comprises a chemoresistive gas microsensor and a circuitry for controlling the temperature and processing the signal supplied by the gas microsensor.

The device 1 comprises a portion 1a in which the microsensor is formed and a portion 1b in which the components of the circuitry are formed. The device 1 is integrated in (and on) a wafer 40 of semiconductor material comprising a substrate 2 of P-type single crystal silicon, defining a surface 10 of the silicon wafer. Astride the substrate 2 there extends a field oxide layer 3 delimiting active area regions of the device. Inside the substrate 2, at an active area region, there is also an N-type pocket 4 housing a component of the circuitry, here an NPN-type transistor 5 having a collector region formed by the pocket 4 and by an $N^+$ contact region 6, a P-type base region 7 and an $N^+$ type emitter region 8.

On top of the surface 10 there extends a dielectric layer 11 (formed, for example, by silicon oxide or BPSG, i.e., Boron Phosphorus Silicon Glass), with a thickness of approximately 1–2 µm. In correspondence with the collector 6, base 7 and emitter 8 regions of the transistor 5, the dielectric layer 11 has respective openings ("vias") 12, 13, 14 for respective metal contacts 15, 16, and 17.

On top of the dielectric layer 11, at the field oxide layer 3, there extends a first metal region, defining a heater 20, of substantially rectangular shape, made of an alloy with a high melting point, preferably of tantalum/aluminum or of tungsten, and having a thickness of approximately 0.1 µm. On the two sides of the heater 20 there are two first contact regions 18 formed at the same time as the metal contacts 15–17 and formed by a double metal layer defining the first metal level, as described in greater detail below. In particular, this double layer comprises the high-melting-point alloy forming the heater 20 and a layer of AlSiCu, with a total thickness of approximately 0.7 µm.

Above the heater 20, the first contact region 18 (at the portion 1a) and the dielectric layer 11 (at the portion 1b) there is a thermal conduction region 25 formed by a stack of layers 23, 24 including a first high thermal conductivity layer 23, of silicon nitride for example, and a second high thermal conductivity layer 24, of silicon carbide for example, superimposed on one another. The two layers 23, 24 have thermal conductivities of approximately 0.19 Watts/cm°K and approximately 3.5 Watts/cm°K respectively (and hence much greater than that of the field oxide layer 3 and of the dielectric layer 11, approximately equal, for both these layers, to 0.015 Watts/cm°K), low electrical conductivity, and an overall thickness of approximately 0.7 µm. The stack of layers 23, 24 also has openings 25a above the first contact regions 18.

On top of the thermal conduction region 25 are disposed second and third contact regions 26, 27, formed from one and the same metal layer (second metal level) and separated from each other by openings 28. The second and third contact regions 26, 27 are formed for example with the same material as the first contact regions 18. The second contact regions 26 have portions extending through the openings 25a as far as the first contact regions 18 for electrical connection of the first contact regions 18 to the circuitry (not shown). As described below, the third contact regions 27 define electrical contacts for the gas sensitive element and in their turn are connected to the circuitry in a manner not shown.

Over the entire surface, apart from the sensor portion 1a, the device 1 further has a dielectric passivation layer 30, having a sealing function. In particular, the dielectric passivation layer 30 covers the second contact regions 26 and part of the third contact regions 27. The dielectric passivation layer 30 has portions extending through the openings 28 to isolate the contact regions 26, 27 electrically with respect to each other. Furthermore, the dielectric passivation layer 30 has a window 30a above the thermal conduction region 25.

Finally, exposed to the external environment, in correspondence with the heater 20 and the thermal conduction region 25, there is a gas sensitive element 34 of substantially rectangular shape and preferably made of tin oxide. The gas sensitive element 34 extends directly in contact with the thermal conduction region 25, inside the window 30a and partially superimposed on the third contact regions 27 which permit its connection to the circuitry.

The heater 20 of the integrated device generates heat, in pulsed manner, preventing the integrated device 1 from reaching a state of thermal equilibrium. In this state, the thermal conduction region 25 produces a preferential path for the heat emitted by the heater 20 towards the sensitive element 34. In fact, in view of the difference in thermal conductivity between the thermal conduction region 25 and the dielectric layer 11 (and the field oxide layer 3), virtually all the heat generated by the heater 20 is conveyed towards the gas sensitive element 34, thereby supplying the desired operating temperature for the gas sensitive element 34 and at the same time preventing the heat from diffusing towards regions underneath and, hence, towards the other active area regions of the device 1.

The manufacturing process of the device 1 described above comprises the following steps.

Initially, the wafer 40 is subjected to standard process steps for the production of electronic components, whether bipolar or MOS, of integrated circuits, in particular the field oxide layer 3, the pocket 4 and the base 7, collector 6 and emitter 8 regions.

Subsequently, the dielectric layer 11 is deposited on the surface 10 of the substrate 2, the openings 12, 13, and 14 for the contacts of the transistor 5 are formed and a first metal high-melting point layer 45 (of tantalum/aluminum or tungsten for example) is deposited and, above that, a second metal layer 46 (of AlSiCu for example) is deposited.

Next, the double layer 45–46 is defined by means of an interconnection mask so as to form the first contact regions 18 and the metal contacts 15–17. At the end of this step the second metal layer 46 still covers the heater 20.

Subsequently, the portion of the second metal layer 46 which covers the heater 20 is removed, leaving in that zone only the high melting point layer 45. Then, with the technique of Plasma Enhanced Chemical Vapour Deposition or PECVD, first a silicon nitride layer and then a silicon carbide layer are deposited, defining the first and second high thermal conductivity layer 23, 24; the openings 25a are then formed in these layers with a photolithography operation.

A third metal layer, of the same material as the second metal layer 46, is then deposited, and is then defined to form the second and third contact regions 26, 27 separated by the openings 28. The second contact regions 26 also fill the openings 25a, forming electrical contacts with the first contact regions 18.

The dielectric passivation layer 30 is then deposited, and is then selectively removed from the uncovered central portion of the thermal conduction region 25 and, partially, from the third contact regions 27 to form the window 30a and the device contact pads (not shown).

Finally, a tin oxide film is deposited by sputtering, and is then defined to form the sensitive element 34 inside the window 30a. The tin oxide also extends partially on the third contact regions 27. to obtain the electrical contact. A catalyst, such as platinum or palladium (not shown), is optionally deposited on the sensitive element 34.

Some advantages of the described sensor and the manufacturing process are as follows.

Firstly, the sensor has low manufacturing costs which are comparable with those of integrated devices, in view of the fact that the manufacturing process described is completely compatible with planar microelectronics technology. Furthermore, the monolithic integration in a single chip of the sensor and of the associated signal processing and control circuits is possible.

The sensor described has superior spatial integration compared with the known solutions which use techniques of anisotropic etching from the front or the back of the substrate. As a result, the sensor is smaller and requires, for its operation, a smaller amount of energy than the known sensors.

Thanks to its high thermal conductivity, directing the majority of the thermal flow towards the gas sensitive element 34, the thermal conduction region 25 enables the desired operating temperatures to be achieved, providing optimal operating conditions for the sensitive element 34, without the need to make excavations in the chip. Furthermore, on the portion of circuitry 1b, the stack of layers 23, 24 promotes the dissipation of the heat generated during operation from the components of the circuitry.

The use of silicon carbide and silicon nitride for the thermal conduction region 25 is particularly advantageous, thanks to the high thermal conductivity of the silicon carbide and thanks to the silicon nitride ability to improve the adhesion of the layer of silicon carbide to the underlying layers and to prevent stress conditions which are possible in the case of adhesion of the silicon carbide directly to the underlying layer.

Finally it will be clear that modifications and variants may be introduced to the device and the process described and illustrated here without thereby departing from the protective scope of the invention as defined in the accompanying claims. In particular, the fact is emphasized that any integration technique can be used, as can any type of substrate, that the electronic components integrated in the chip may be of the bipolar and the MOS type and that the type of conductivity of the various regions may vary with respect to that shown.

What is claimed is:

1. An integrated semiconductor device, comprising a chemoresistive gas microsensor and including a heater element disposed on top of a semiconductor material body and a gas sensitive element disposed on, and electrically isolated from, said heater element, wherein said device comprises a high thermal conductivity region, interposed between said heater element and said gas sensitive element and defining a preferential path towards said gas sensitive element for heat emitted by said heater, and a thermally insulating region interposed between said heater element and said semiconductor material body and having thermal conductivity lower than said high thermal conductivity region.

2. The device according to claim 1 wherein said thermally insulating region comprises a surface insulating layer and a field oxide layer disposed astride a portion of the surface of said semiconductor material body.

3. The device according to claim 1, further comprising first and second high thermal conductivity layers, superimposed one with respect to the other and defining at least said high thermal conductivity region.

4. The device according to claim 3 wherein said first high thermal conductivity layer is a layer of silicon nitride, disposed in contact with said heater element, and said second high thermal conductivity layer is a layer of silicon carbide.

5. The device according to claim 1 wherein said heater element includes tantalum/aluminum.

6. The device according to claim 3, further comprising:
   first contact regions of electrically conductive material, disposed on a first level as, laterally and in contact with said heater element, said first and second high thermal conductivity layers, and having first windows at said first contact regions;
   second contact regions of electrically conductive material, disposed above said first and second high thermal conductivity layers and in contact with said first contact regions through said first windows; and
   third contact regions of electrically conductive material, disposed above said first and second high thermal conductivity layers, on a second level as said second contact regions and physically separated therefrom, said gas sensitive element being disposed in contact with said third contact regions.

7. A semiconductor device for chemical sensing and having a first and a second portion, comprising:
   a semiconductor material substrate;
   a thermally insulating element deposited over the semiconductor material substrate;
   a heater element deposited over the first portion of the thermally insulating element;
   a thermally conductive element deposited at least over the heater element, said thermally conductive element having thermal conductivity higher than the thermally insulating element; and
   a chemically sensitive element deposited over part of the thermally conductive element, said chemically sensitive element defining a preferential thermal path for emitting heat generated by the heater element.

8. The device of claim 7 wherein the thermally insulating element comprises a first dielectric layer deposited over the substrate in the first portion and a second dielectric layer deposited over the first dielectric layer and over the substrate in the second portion.

9. The device of claim 7 wherein the thermally conductive element comprises a stack of first and second high thermally conductive layers, the first high thermally conductive layer contacting with the heater element and comprising silicon nitride, and the second high thermally conductive layer comprising silicon carbide.

10. The device of claim 7 wherein the heater element comprises high melting point metal, in particular, a tantalum/aluminum alloy.

11. The device of claim 7, further comprising:

patterned first contact regions deposited over the heater element, said thermally conductive element being deposited over the first contact regions and having first openings over the first contact regions;

patterned second contact regions deposited over the thermally conductive element, said second contact regions contacting said first contact regions through said first openings;

patterned third contact regions deposited over the thermally conductive element, said third contact regions being electrically isolated from the second contact regions by second openings and being partially covered by said chemically sensitive element; and a passivation layer deposited at least over the second portion of the device, the second contact regions, the second openings, and part of the third contact regions.

12. The device of claim 7, further comprising a control element having a bipolar or a MOS transistor formed in the second portion of the substrate.

* * * * *